US00PP08709P

United States Patent [19]

Stravers

[11] Patent Number: Plant 8,709

[45] Date of Patent: May 3, 1994

[54] GERBERA PLANT 'TERKITOS'

[75] Inventor: Johannes J. M. Stravers, Kudelstaart, Netherlands

[73] Assignee: Terra Nigra B.V., Iepenlaan, Netherlands

[21] Appl. No.: 942,281

[22] Filed: Sep. 9, 1992

[51] Int. Cl.[5] ..... A01H 5/00
[52] U.S. Cl. ..... Plt./68.1
[58] Field of Search ..... Plt. 68.1

*Primary Examiner*—James R. Feyrer

[57] ABSTRACT

A new and distinct member of *Gerbera jamesonni* plant named 'Terkitos' which is particularly distinguished by its double flower type and a specific intense lilac-purple color of the ray florets, a green disc floret, the outermost florets of which show white stigmas and the middle flowers of which show yellow anthers, purple perianth lobe color and 100 mm overall flower diameter.

1 Drawing Sheet

BACKGROUND OF THE INVENTION

The present invention comprises a new and distinct cultivar of *Gerbera jamesonni*, referred to by the cultivar name 'Terkitos'. 'Terkitos' was originated from a hybridization program in De Kwakel, The Netherlands in 1988. The female parent was unnamed seedling 86.91, and the male parent was unnamed seedling TN 10. Female parent 86.91 has a higher production, shorter stems, smaller flower diameter, and a less intense purple color than 'Terkitos'. Of TN 10 is no description available. Both parent plants were not available to others outside the company, and they weren't registered in the USA. The new cultivar was selected by me from the progeny of the stated parentage on or about November 1988. The first asexual reproduction of 'Terkitos' was accomplished when vegetative cuttings were taken on April 1989 in De Kwakel. The new cultivar is presently being propagated by cuttings and tissue culture. Horticultural examination of selected units initiated November 1989 has demonstrated that the combination of characteristics as herein disclosed for 'Terkitos' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terkitos', which in combination distiguish this Gerbera from its parents and all other varieties of which I am aware:

1. Type: Semi-double.
2. Color of ray floret: Distinctive purple.
3. Color of disc floret: Distinctive green.
4. Color of perianthy lobe: Purple.
5. Diameter of flower head: Medium 100 mm.

Of the many commercial cultivars known to me, there is no cultivar similar in comparison to 'Terkitos'.

BRIEF DESCRIPTION OF THE DRAWING

The accompanying photographic drawing shows typical flower characteristics nearly true as possible. In the following description, color references are made to The Royal Horticultural Society Color Chart (RHS).

The color values were determined at 09:30 a.m. on Feb. 25, 1990 under natural light at De Kwakel.

BOTANICAL DESCRIPTION OF THE PLANT

Botanical: *Gerbera jamessoni* cv 'Terkitos'.

INFLORESCENCE

A. Capitulum:
*Form.*—Flat shaped.
*Type.*—Semi-double.
*Diameter across face.*—100 mm.

B. Corolla of ray florets:
*Color (general tonality from a distance of* 3 *meters)*-.—Purple.
*Color (topside).*—RHS 57C.
*Color (bottom).*—RHS 64D.

C. Corolla of disc florets:
*Color (mature).*—Purple RHS 57C.
*Color (immature).*—Purple RHS 57C.

D. Reproductive organs:
*Stigma.*—White RHS 155B.
*Anthers.*—Dark yellow RHS 17B.
*Pappus.*—Yellow RHS 11B.

PLANT

A. General appearance:
*Height.*—40 cm.

B. Foliage:
*Color (abaxial).*—RHS 147A.
*Color (adaxial).*—RHS 138B.
*Shape.*—The angle of apex: right angle. The shape of apex: rounded. The margin of lobes: sinuate.

C. Disease resistance: No special disease resistance.

OTHER CHARACTERISTICS

The vigor of 'Terkitos' is standard for a Gerbera cultivar (height about 40 cm). During springtime it takes about 19 weeks before flowering. During autumn it will take about 3–4 weeks longer. On annual basis, "Terkitos' will produce an average of 23 flowers when growing in soil, and 27 when growing in rockwool slabs. Flowering is whole year round with a higher flower production during spring, and lower during autumn. The habit is a basal rosette which is typical for the gerbera cutflower industry. The life of the cutflowers is about 8 days.

The following traits have been repeatedly observed and are determined to be basic characteristics of 'Terkitos', which in combination distinguish this Gerbera as a new and distinct cultivar.

Leaf blade:

*Length.*—Medium.
*Width.*—Medium.
*Thickness.*—Medium.
*Blistering.*—Weak.
*Pubescence.*—On upper side (midrib excluded) of the leaf blade is medium.
*Depth of cuts or incisions in leaf.*—Basal part: Deep. Central part: Shallow. Distal part: Shallow.
*Color.*—Upper side of the leaf blade is medium green (RHS 137A).
*Glossiness on upper side.*—Medium.
*Angle of apex.*—Right angle.
*Shape of apex.*—Rounded.
*Margin of lobes.*—Sinuate.
*Extensions of margin.*—Absent.
*Petiole length.*—Medium (10 cm).
*Petiole anthocyanin coloration.*—Medium.

At the time of flowering, the length of an average mature leaf is 36 cm which is a short-medium length for Gerbera plants. The width of an average mature leaf is 15 cm which is small-medium for Gerbera plants.

Peduncle:

*Length.*—Medium (60 cm).
*Cross section.*—Elliptic.
*Tendency to fasciation.*—Present.
*Thickness.*—Medium.
*Strength.*—Strong.
*Pubescence.*—Medium.
*Color.*—Medium green.
*Anthocyanin coloration.*—At base: Medium. At top: Present.
*Involucral bracts.*—Present.

Flower head:

*Type.*—Semi-double.
*Diameter.*—Medium (approx. 100 mm).
*Involucre.*—Height: Medium (15 mm). Diameter: Medium. Number of bracts: Medium. Longitudinal axis of bracts of inner rows: Reflexing. Anthocyanin: Absent. Pubescence: Medium.
*Ray florets.*—Number: Medium. Shape: Narrow elliptic. Longitudinal axis outer row: Reflexing. Longitudinal axis inner row: Straight.
*Outer ray florets.*—Cross section: Flat. Length: Medium (40 mm). Width: Medium. Longitudinal folding: Medium. Angle of apex: Right. Shape of apex: Pointed. Incisions of apex: Present. Number: One. Depth: Medium. Length of free petals: Long. Color distribution on inner side: Uniform. Edge of different color: Absent. Striation: Absent. Claw spot: Absent.

Disc florets:

*Diameter.*—Medium.
*Main color perianth lobes.*—Purple for both female (RHS 57B) and male flowers (RHS 57B).

Reproductive parts

*Stigma.*—Main color white (RHS 155B).
*Anthers.*—Main color dark yellow (RHS 17B). Color of top relative to other parts is lighter Longitudinal striping: Present.
*Pappus.*—Main color yellow (RHS 11B). Color of the top relative to other parts is identical. Orientation: Level of top relative to closed disc florets is the same.
*Fertility.*—Fertility is good; reasonable seed production.

I claim:

1. A new and distinct cultivar of *Gerbera jamesonni* plant named 'Terkitos', as illustrated and described, distinguished by its double flower type and a specific intense lilac-purple color of the ray florets, a green disc floret, the outermost florets of which show white stigmas and the middle flowers of which show yellow anthers, purple perianth lobe color and 100 mm overall flower diameter.

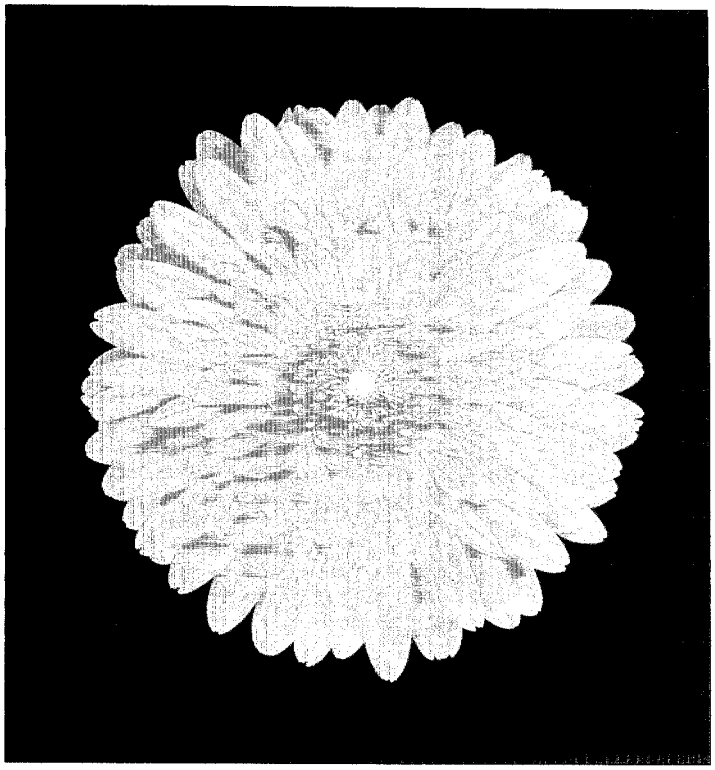

* * * * *